US011006693B2

(12) United States Patent
Hanft

(10) Patent No.: US 11,006,693 B2
(45) Date of Patent: May 18, 2021

(54) ARTICLES OF FOOTWEAR FOR INHIBITING AND TREATING INJURIES

(71) Applicant: Jason R. Hanft, South Miami, FL (US)

(72) Inventor: Jason R. Hanft, South Miami, FL (US)

(\*) Notice: Subject to any disclaimer, the term of this patent is extended or adjusted under 35 U.S.C. 154(b) by 475 days.

(21) Appl. No.: 15/884,083

(22) Filed: Jan. 30, 2018

(65) Prior Publication Data
US 2018/0235312 A1 Aug. 23, 2018

Related U.S. Application Data

(60) Provisional application No. 62/452,831, filed on Jan. 31, 2017, provisional application No. 62/452,832, filed on Jan. 31, 2017.

(51) Int. Cl.
| | |
|---|---|
| *A43B 7/00* | (2006.01) |
| *A43B 13/16* | (2006.01) |
| *A43B 23/02* | (2006.01) |
| *A43B 7/20* | (2006.01) |
| *A43B 7/32* | (2006.01) |
| *B32B 5/18* | (2006.01) |
| *B32B 25/04* | (2006.01) |
| *B32B 25/16* | (2006.01) |
| *A61F 5/01* | (2006.01) |
| *A43B 3/02* | (2006.01) |
| *A43B 7/14* | (2006.01) |

(52) U.S. Cl.
CPC .................. *A43B 7/00* (2013.01); *A43B 3/02* (2013.01); *A43B 7/147* (2013.01); *A43B 7/20* (2013.01); *A43B 7/32* (2013.01); *A43B 13/16* (2013.01); *A43B 23/0275* (2013.01); *A43B 23/0295* (2013.01); *A61F 5/0111* (2013.01); *A61F 5/0195* (2013.01); *B32B 5/18* (2013.01); *B32B 25/042* (2013.01); *B32B 25/045* (2013.01); *B32B 25/16* (2013.01); *B32B 2307/724* (2013.01); *B32B 2437/02* (2013.01)

(58) Field of Classification Search
CPC .. A43B 7/00; A43B 7/147; A43B 7/20; A43B 13/16; A43B 23/0275; A43B 3/02; A43B 7/32; A43B 23/0295; A61F 5/0111; A61F 5/0195
USPC ........................... 36/109, 89, 110, 69, 57, 58
See application file for complete search history.

(56) References Cited

U.S. PATENT DOCUMENTS

| | | | | |
|---|---|---|---|---|
| 1,522,256 | A * | 1/1925 | Meyers | ..................... A43B 7/00 36/89 |
| 3,878,626 | A * | 4/1975 | Isman | ................... A43B 1/0054 36/15 |
| 4,267,650 | A * | 5/1981 | Bauer | ..................... A43B 13/36 36/101 |
| 5,317,820 | A | 6/1994 | Bell et al. | |
| 5,425,701 | A | 6/1995 | Oster et al. | |
| 6,170,175 | B1 * | 1/2001 | Funk | ........................ A43B 5/04 36/115 |

(Continued)

OTHER PUBLICATIONS

International Search Report and the Written Opinion of the International Searching Authority dated Apr. 19, 2018, 9 pages.

*Primary Examiner* — Ted Kavanaugh
(74) *Attorney, Agent, or Firm* — Richard P. Gilly, Esq.; Archer & Greiner, P.C.

(57) ABSTRACT

Articles of footwear for protecting injured, at-risk, or post-surgical feet and ankles include upper and/or sole structures that offload the feet and ankles when standing and/or walking.

15 Claims, 10 Drawing Sheets

(56) References Cited

U.S. PATENT DOCUMENTS

| | | | |
|---|---|---|---|
| 8,225,532 B2* | 7/2012 | Chen | A43B 1/0009 |
| | | | 36/103 |
| 2009/0287127 A1 | 11/2009 | Hu et al. | |
| 2014/0316316 A1* | 10/2014 | Andrews | A61F 13/04 |
| | | | 602/12 |
| 2015/0164179 A1* | 6/2015 | Walborn | A43B 13/145 |
| | | | 36/25 R |
| 2016/0184533 A1 | 6/2016 | Mayer | |
| 2016/0213506 A1 | 7/2016 | Chen | |
| 2016/0324666 A1* | 11/2016 | Barberio | A61F 5/0118 |
| 2018/0104081 A1* | 4/2018 | Salvatelli | A61F 5/0195 |

* cited by examiner

ARTICLES OF FOOTWEAR FOR INHIBITING AND TREATING INJURIES

TECHNICAL FIELD

Embodiments of the present disclosure relate generally to articles of footwear for protecting injured, at-risk, or post-surgical feet and ankles, and more specifically to articles of footwear for wearers having conditions or leg and foot complications associated with conditions that may be treated or managed by offloading the feet and ankles when standing or walking (for example, diabetes neuropathy, vascular disease, arthritis, neuroarthropathy, post-surgical, and post-amputation).

BACKGROUND

Certain types of articles of footwear, commonly referred to as "walking boots", are designed at least partially offload forces applied to the feet and ankles of wearers when standing or walking. Such offloading facilitates treating or managing various conditions or leg and foot complications associated with various conditions (for example, diabetes, neuropathy, vascular disease, arthritis, neuroarthropathy, post-surgical, and post-amputation). However, such articles of footwear have limited effectiveness and/or are cumbersome or even painful, which frequently causes individuals to refrain from wearing the articles of footwear.

SUMMARY

An article of footwear configured to be worn on a lower leg and foot of a wearer, including: an upper including a main body, the main body including: a posterior brace configured to be disposed posteriorly relative to the lower leg of the wearer, the posterior brace configured to stabilize the heel of the wearer; and at least one side brace coupled to the posterior brace, the side brace configured to be disposed medially or laterally relative to the lower leg of the wearer, the side brace configured to decelerate the foot of the wearer during heel strike.

The article of footwear, wherein the upper further includes a closure coupled to at least one of the posterior brace and the side brace, the closure including an anterior portion that is movable and configured to permit entry and egress of the leg of the wearer from the article of footwear.

The article of footwear, wherein the closure further includes a superior brace configured to support the patellar tendon or the tibial tuberosity of the leg of the wearer.

The article of footwear, wherein the upper further includes a superior brace configured to support the patellar tendon or the tibial tuberosity of the leg of the wearer.

The article of footwear, wherein the posterior brace includes: a posterior heel portion configured to be disposed posteriorly of the heel of the wearer; and an inferior heel portion configured to be disposed inferiorly of the heel of the wearer.

The article of footwear, wherein the upper includes: an inner layer including a breathable, low-friction material; an intermediate layer disposed outwardly of the inner layer, and the intermediate layer including a semi-rigid material; and an outer layer disposed outwardly of the intermediate layer.

The article of footwear, wherein the upper further includes a flexible material disposed inwardly of the side brace.

The article of footwear, wherein the side brace includes: a first portion extending anteriorly and inferiorly away from the posterior brace; and a second portion coupled to the first portion, the second portion extending posteriorly and inferiorly away from the first portion.

The article of footwear, wherein the first portion has a first flexural modulus, the second portion has a second flexural modulus, and the second flexural modulus is less than the first flexural modulus.

The article of footwear, wherein the upper further includes a flexible material disposed inwardly of the side brace, the flexible material including: a first portion disposed superiorly relative to the first portion of the side brace; a second portion disposed between the first portion of the side brace and the second portion of the side brace; and a third portion disposed inferiorly relative to the second portion of the side brace.

The article of footwear, further including a sole coupled to the upper, the sole including: an outsole configured to engage the ground, the outsole including a body defining a cavity; and an insole configured to support the foot of the wearer, the insole coupled to the outsole within the cavity; wherein at least one of the outsole and the insole form a securing structure, the securing structure including a protrusion for engaging the other of the outsole and the insole and securing the insole to the outsole.

An article of footwear according to another embodiment of the present disclosure includes an upper including a posterior brace configured to be disposed posteriorly relative to the lower leg of the wearer, the posterior brace configured to stabilize the heel of the wearer; and a superior brace coupled to the posterior brace, the superior brace configured to support the patellar tendon or the tibial tuberosity of the leg of the wearer.

The article of footwear, wherein the upper further includes: a main body including the posterior brace; and a closure coupled to the main body, the closure including an anterior portion that is movable and configured to permit entry and egress of the leg of the wearer from the article of footwear.

The article of footwear, wherein the closure includes the superior brace.

The article of footwear, wherein the upper includes: an inner layer including a breathable, low-friction material; an intermediate layer disposed outwardly of the inner layer, and the intermediate layer including a semi-rigid material; and an outer layer disposed outwardly of the intermediate layer.

The article of footwear, wherein the inner layer, the intermediate layer, and the outer layer define the posterior brace.

The article of footwear, wherein the posterior brace includes: a lateral portion; and a medial portion spaced apart from the lateral portion.

An article of footwear according to yet another embodiment of the present disclosure includes an upper including: at least one side brace configured to be disposed medially or laterally relative to the lower leg of the wearer, the side brace configured to decelerate the foot of the wearer during heel strike; and a superior brace coupled to the side brace, the superior brace configured to support the patellar tendon or the tibial tuberosity of the leg of the wearer.

The article of footwear, wherein the upper further includes: a main body including the side brace; and a closure coupled to the main body, the closure including an anterior portion that is movable and configured to permit entry and egress of the leg of the wearer from the article of footwear.

The article of footwear, wherein the closure includes the superior brace.

The article of footwear, wherein the upper further includes a flexible material disposed inwardly of the side brace.

The article of footwear, wherein further including a sole coupled to the upper, the sole including: an outsole configured to engage the ground, the outsole including a body defining a cavity; and an insole configured to support the foot of the wearer, the insole interference fittingly engaging the outsole in the cavity to secure the insole to the outsole.

An article of footwear according to yet another embodiment of the present disclosure includes an outsole configured to engage the ground, the outsole including a body defining a cavity; and an insole configured to support the foot of the wearer, the insole interference fittingly engaging the outsole in the cavity to secure the insole to the outsole.

The article of footwear, wherein at least one of the outsole and the insole include a protrusion interference fittingly engaging the other of the outsole and the insole to secure the insole to the outsole.

The article of footwear, wherein the outsole includes the protrusion.

The article of footwear, wherein the insole includes a recess for interference fittingly engaging the protrusion.

The article of footwear, wherein the outsole further includes: a cavity inferior surface; and a cavity side surface defining the cavity together with the cavity inferior surface, the cavity side surface including the protrusion.

The article of footwear, further including an upper coupled to the outsole.

The article of footwear, wherein the upper includes at least one side brace configured to be disposed medially or laterally relative to a lower leg of the wearer, the side brace configured to decelerate the foot of the wearer during heel strike.

The article of footwear, wherein the side brace includes: a first portion extending anteriorly and inferiorly away from a posterior portion of the upper; and a second portion coupled to the first portion, the second portion extending posteriorly and inferiorly away from the first portion.

The article of footwear, wherein the first portion has a first flexural modulus, the second portion has a second flexural modulus, and the second flexural modulus is less than the first flexural modulus.

An article of footwear according to yet another embodiment of the present disclosure includes an outsole configured to engage the ground, the outsole including a body defining a cavity; and an insole configured to support the foot of the wearer, the insole coupled to the outsole within the cavity; wherein at least one of the outsole and the insole form a securing structure, the securing structure including a protrusion for engaging the other of the outsole and the insole and securing the insole to the outsole.

The article of footwear, wherein the outsole includes the protrusion.

The article of footwear, wherein the insole includes a recess in which the protrusion is disposed.

The article of footwear, wherein the outsole further includes: a cavity inferior surface; and a cavity side surface defining the cavity together with the cavity inferior surface, the cavity side surface including the protrusion.

The article of footwear, further including an upper coupled to the outsole.

The article of footwear, wherein the upper includes at least one side brace configured to be disposed medially or laterally relative to a lower leg of the wearer, the side brace configured to decelerate the foot of the wearer during heel strike.

The article of footwear, wherein the side brace includes: a first portion extending anteriorly and inferiorly away from a posterior portion of the upper; and a second portion coupled to the first portion, the second portion extending posteriorly and inferiorly away from the first portion.

The article of footwear, wherein the first portion has a first flexural modulus, the second portion has a second flexural modulus, and the second flexural modulus is less than the first flexural modulus.

An article of footwear according to yet another embodiment of the present disclosure includes an outsole for receiving an insole, the outsole including: a body defining a cavity, the body including a projection extending into the cavity and being sized to interference fittingly engage the insole to secure the insole to the outsole.

The article of footwear, wherein the projection includes an arcuate surface.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
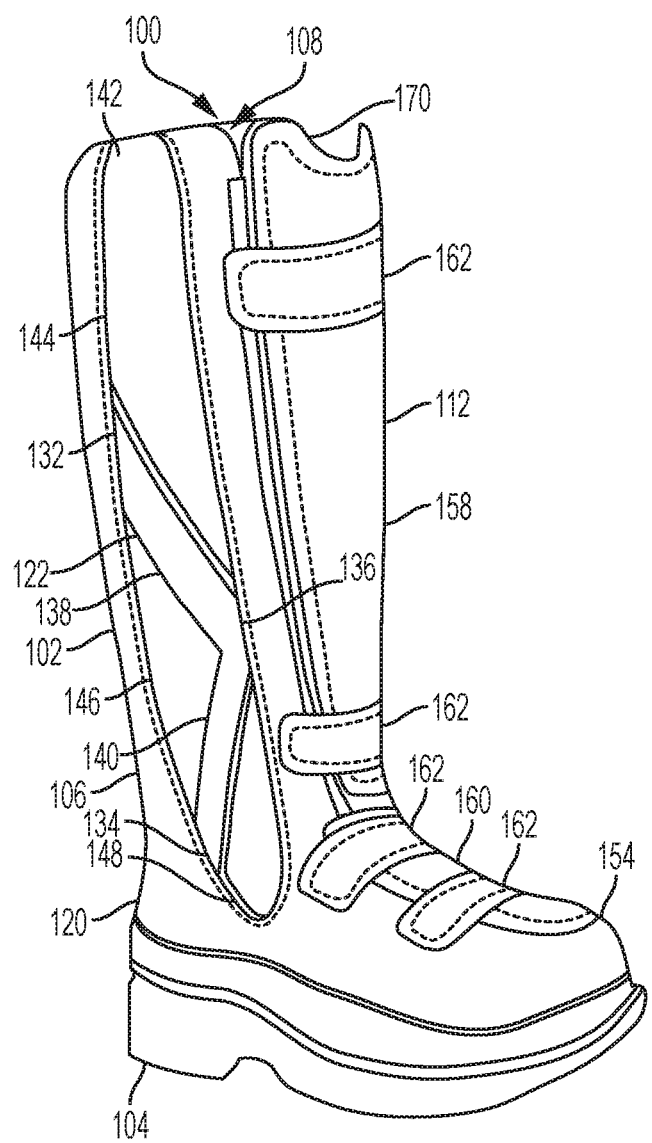
FIG. 1 illustrates a front perspective view of an embodiment of an article of footwear according to the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

It should be understood that the anatomical terms "superior", "inferior", "anterior", "posterior", "medial", and "lateral", as well as variations thereof (for example, "superiorly" and the like) are used to describe relative positions of features of articles of footwear. Such terms refer to anatomical reference directions when an article of footwear is positioned on a wearer's leg in a typical orientation. More specifically, "superior" refers to a direction generally extending from the feet toward the knee, "inferior" refers to a direction generally extending from the knee toward the feet, "anterior" refers to a direction generally extending from the heel to the toes, "posterior" refers to a direction generally extending from the toes to the heel, "medial" refers to directions generally extending from the small toes to the large toes, "lateral" refers to directions generally extending from the large toes to the small toes, "outward" refers to directions generally extending away from the leg, and "inward" refers to directions generally extending toward the leg.

Figure 2:
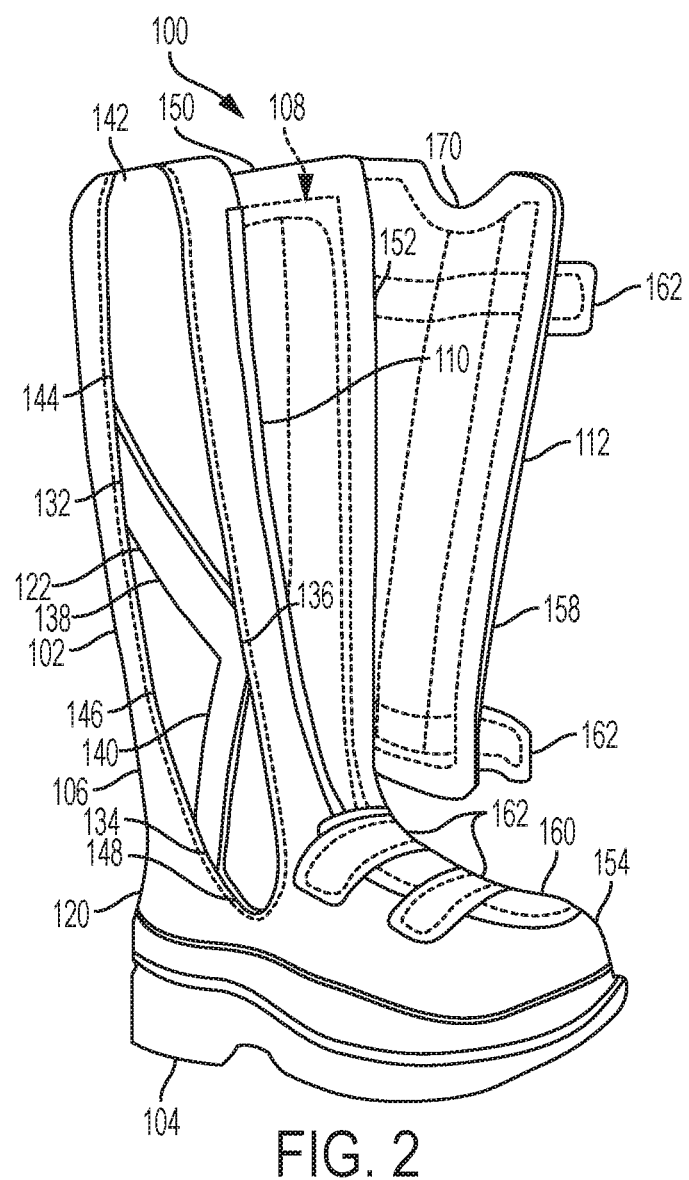
FIG. 2 illustrates another front perspective view of the article of footwear of FIG. 1 with an anterior closure in an open position.
Figure 3:
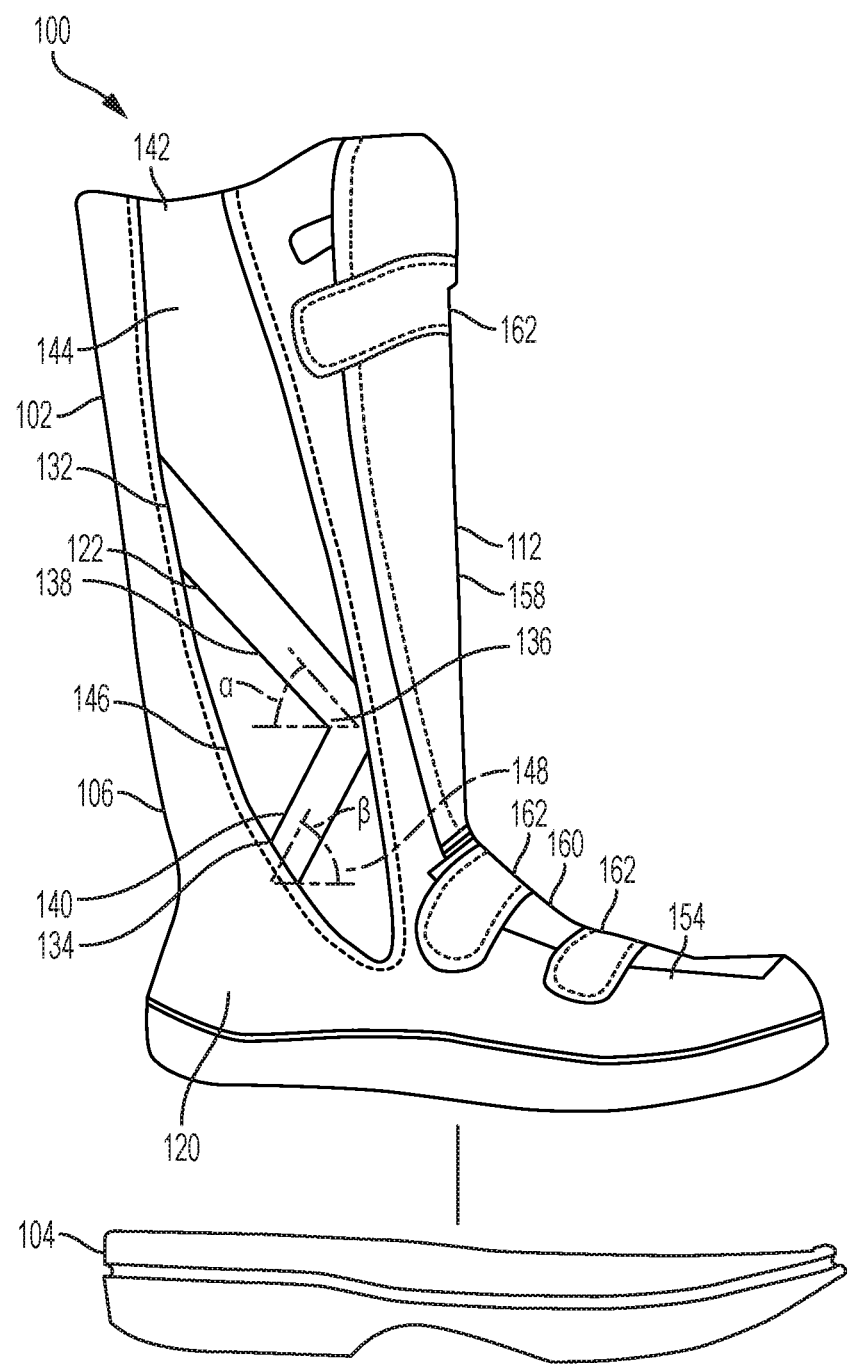
FIG. 3 illustrates a partially exploded lateral side view of the article of footwear of FIG. 1.

Referring to FIGS. 1-3, an embodiment of an article of footwear 100 is configured to receive and be worn on the leg of a wearer. The article of footwear 100 generally includes an upper 102 that is coupled to a sole 104. As described in further detail below, the upper 102 and the sole 104 include features that protect the leg of the wearer from the environment and significantly reduce forces acting on the foot and ankle of the wearer when standing and walking. As such, the article of footwear 100 facilitates post-surgical healing, non-surgical wound healing, and inhibiting wound formation for some types of wearers (wearers having diabetes, neuropathy, vascular disease, arthritis, neuroarthropathy, and the like).

Upper

Referring to FIGS. 1-5, the upper 102 generally includes a main body 106 that defines a chamber 108 for receiving the leg of the wearer. The upper 102 also includes an opening 110 coupled to the chamber 108. The opening 110 permits entrance of the leg of the wearer to the chamber 108 and egress of the leg of the wearer from the chamber 108. The upper 102 further includes a closure 112 that is movably coupled to the main body 106 to selectively enclose a portion of the opening 110 and to assist in securing the article of footwear 100 to the leg of the wearer.

Figure 5:
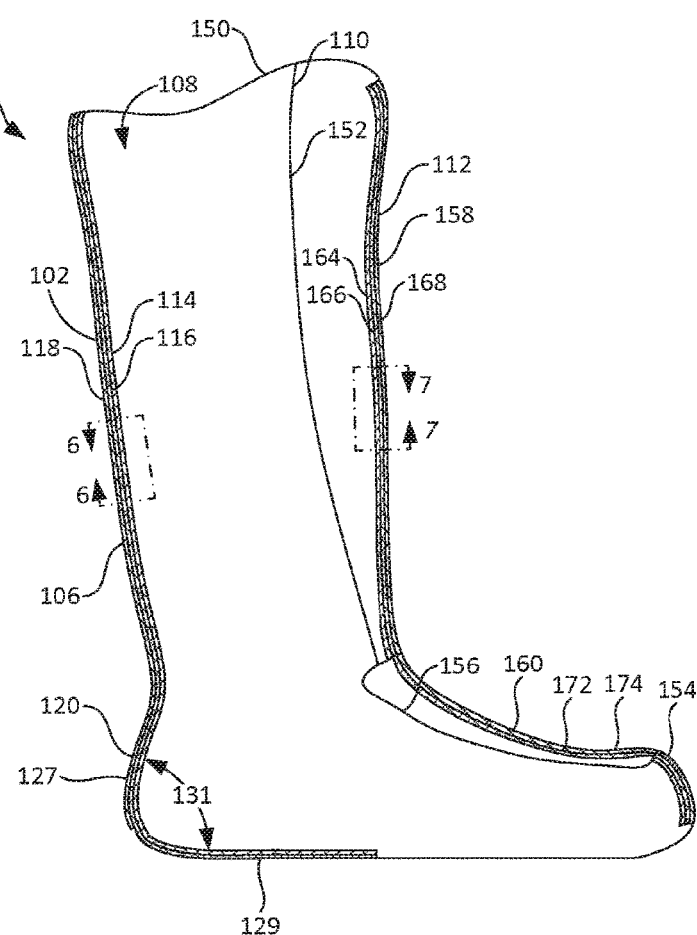
FIG. 5 illustrates a side sectional view of the article of footwear along line 5-5 of FIG. 4.
Figure 6:
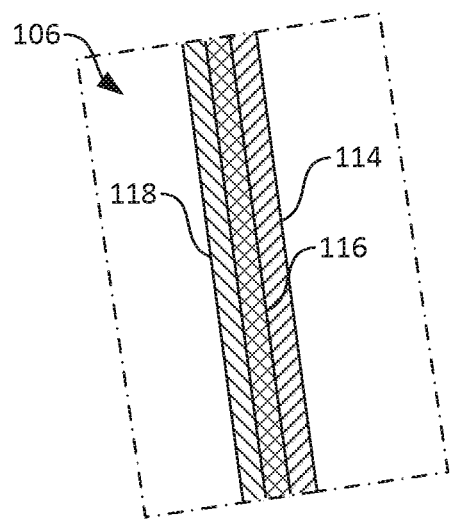
FIG. 6 illustrates a detail view of the article of footwear within line 6-6 of FIG. 5.

Referring specifically to FIGS. 5 and 6, in some embodiments the main body 106 includes one or more portions having multiple layers. More specifically, the main body 106 may include an inner layer 114, an intermediate layer 116 disposed outwardly of the inner layer 114, and an outer layer 118 disposed outwardly of the intermediate layer 116. The main body inner layer 114 may be a breathable, low-friction material. The inner layer 114 may be formed of one or more materials having a static coefficient of friction against steel in range of 0.01 to 1.5, more specifically in range of 0.01 to 1.0, and even more specifically in a range of 0.01 to 0.5. As a specific example, the inner layer 114 may be formed of a polymer, such as a synthetic rubber, for example polychloroprene or neoprene. In some embodiments, the inner layer 114 may be formed of a material having an air permeability similar to that of polychloroprene or neoprene. The main body intermediate layer 116 may be a semi-rigid material. The intermediate layer 116 may be formed of one or more materials having an elastic modulus in a range of 0.5 to 4.6 GPa, more specifically in a range of 1.8 to 4.6 GPa, and more specifically in a range of 3.2 to 4.6 GPa. As a specific example, the intermediate layer 116 may be formed of a polymer, such as a polymer foam or a rubber. The main body outer layer 118 may be formed of one or more of various materials that may provide various aesthetic and/or functional characteristics (for example, water resistance), such as polymers (for example, rubber), fabrics, and/or leather.

The main body 106 also includes braces that reduce forces acting on the foot and ankle of the wearer when standing and walking. Move specifically, in some embodiments, the main body 106 includes a posterior brace 120 that is configured to be disposed posteriorly relative to the lower leg of the wearer (that is, posteriorly relative to the calf of the wearer). The main body 106 also includes a lateral side brace 122 and a medial side brace 124 configured to be disposed laterally and medially, respectively, relative to the lower leg of the wearer.

The posterior brace 120 is configured to stabilize the heel of the wearer. In some embodiments, the posterior brace 120 is configured to hold the leg at a 90 degree angle relative to the foot. In some embodiments, the posterior brace 120 is configured to decelerate the foot when the sole 104 contacts the ground and accelerate the foot during propulsion. In some embodiments, the posterior brace 120 is configured to stabilize the ankle and the subtalar joint by inhibiting both ankle motion and inversion and eversion motion of the subtalar joint. In some embodiments, the posterior brace 120 increases the rigidity and stability of the sole 104. In some embodiments, the posterior brace 120 is defined by the inner layer 114, the intermediate layer 116, and the outer layer 118 of the main body 106. In some embodiments and referring specifically to FIG. 4, the posterior brace 120 includes a lateral portion 128 and medial portion 126 spaced apart from the lateral portion 128 by a gap 130. The gap 130 facilitates expansion and compression of the lower leg of the wearer. In some embodiments, no solid material is present in the gap 130. In some embodiments, the gap 130 has a size in a range of 2 mm to 2 cm. In some embodiments and referring specifically to FIG. 5, the posterior brace 120 includes a posterior heel portion 127 that is configured to be disposed posteriorly of the heel of the wearer and an inferior heel portion 129 that is configured to be disposed inferiorly of the heel of the wearer. In some embodiments, the inferior heel portion 129 terminates posteriorly relative to the metatarsus of the wearer. In some embodiments, an angle 131 between the posterior heel portion 127 and the inferior heel portion 129 is an acute angle. More specifically, the angle 131 may be in a range of 89.9 degrees to 75.0 degrees, more specifically in a range of 89.9 degrees to 60.0 degrees, and more specifically in a range of 89.9 degrees to 40.0 degrees. In some embodiments, such angles facilitate upper ankle dorsiflexion.

Figure 4:
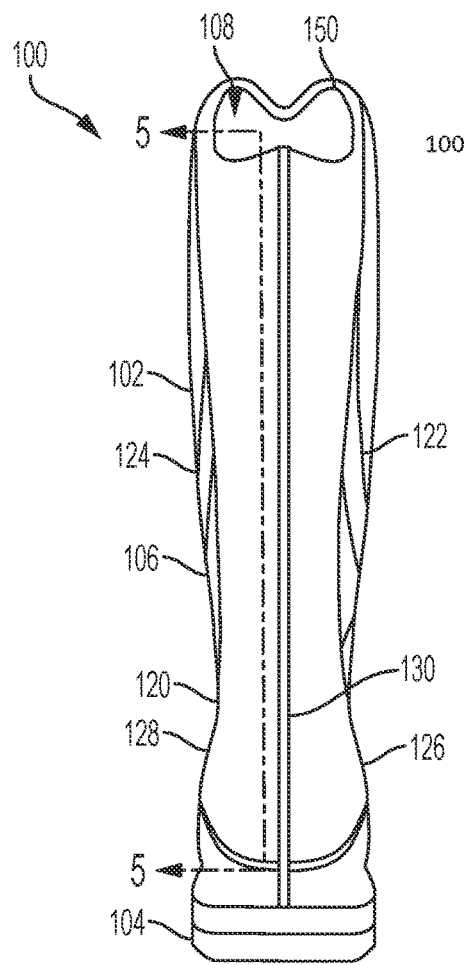
FIG. 4 illustrates a rear view of the article of footwear of FIG. 1.
Figure 8:
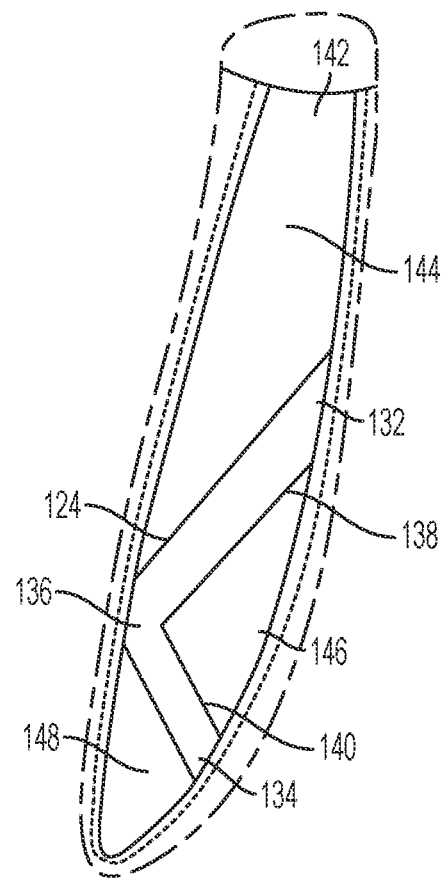
FIG. 8 illustrates a partial medial side view of the article of footwear of FIG. 1.
Figure 9:
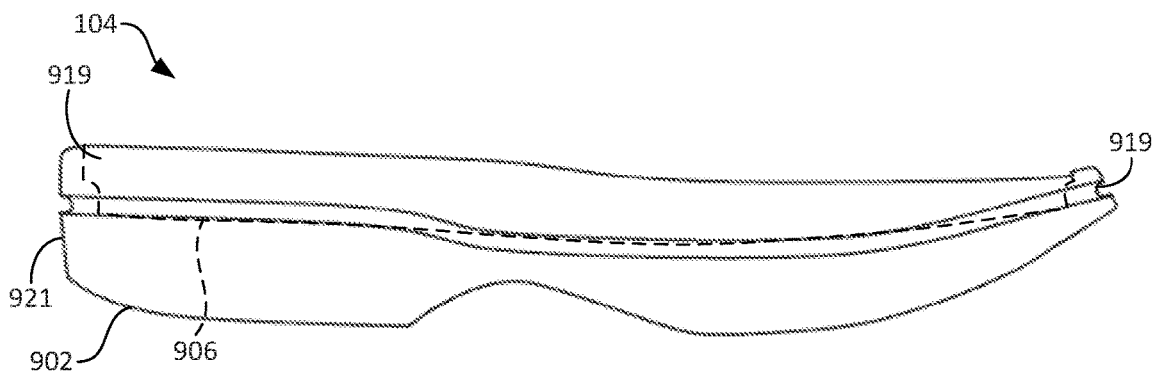
FIG. 9 illustrates a side view of an embodiment of a sole of an article of footwear according to the present disclosure.
Figure 10:
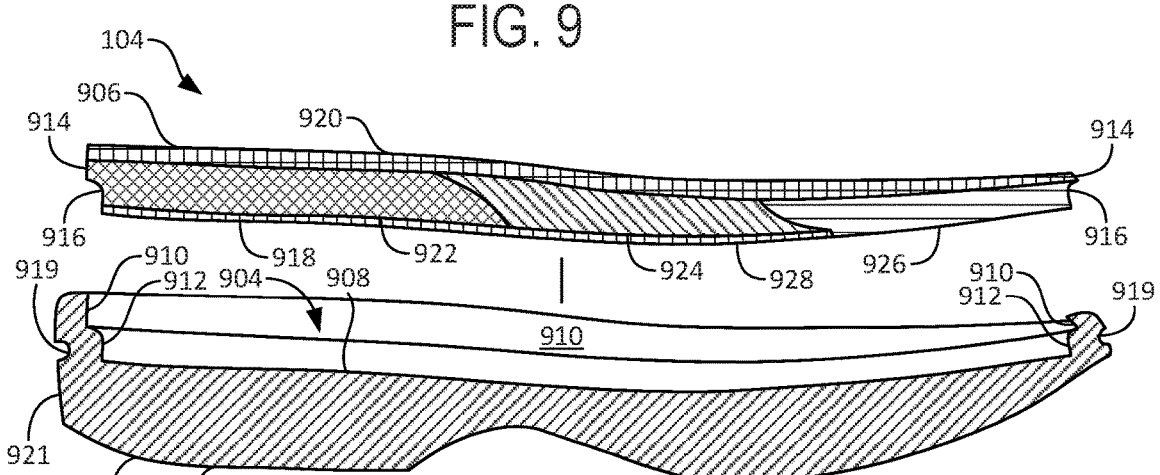
FIG. 10 illustrates a partially exploded side sectional view of the sole of FIG. 9.
Figure 11:
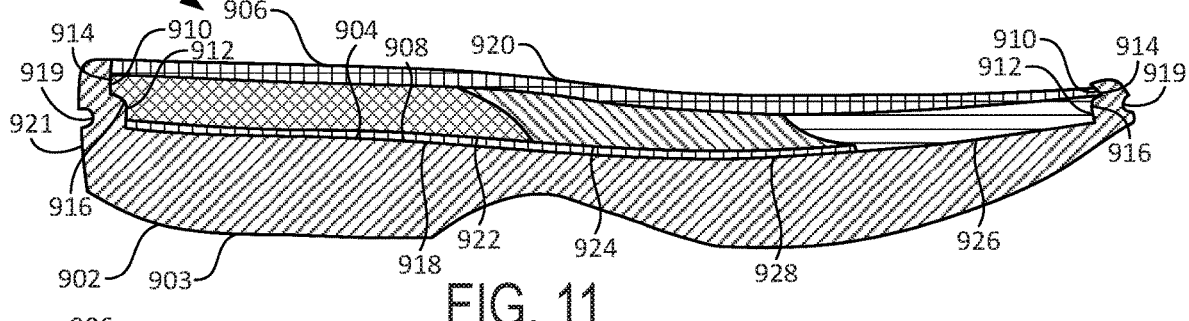
FIG. 11 illustrates a side sectional view of the sole of FIG. 9.
Figure 12:
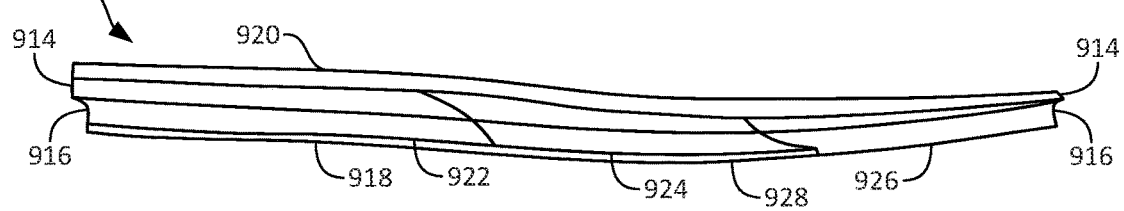
FIG. 12 illustrates a side view of an insole of the sole of FIG. 9.
Figure 13:
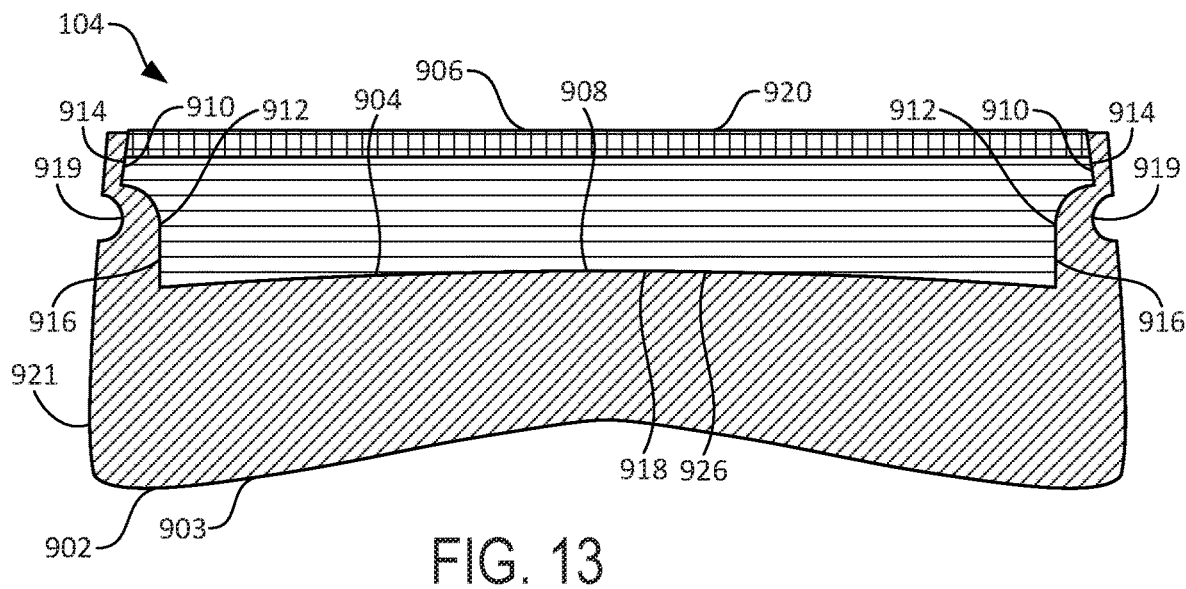
FIG. 13 illustrates a front sectional view of the sole along line 13-13 of FIG. 9.
Figure 14:
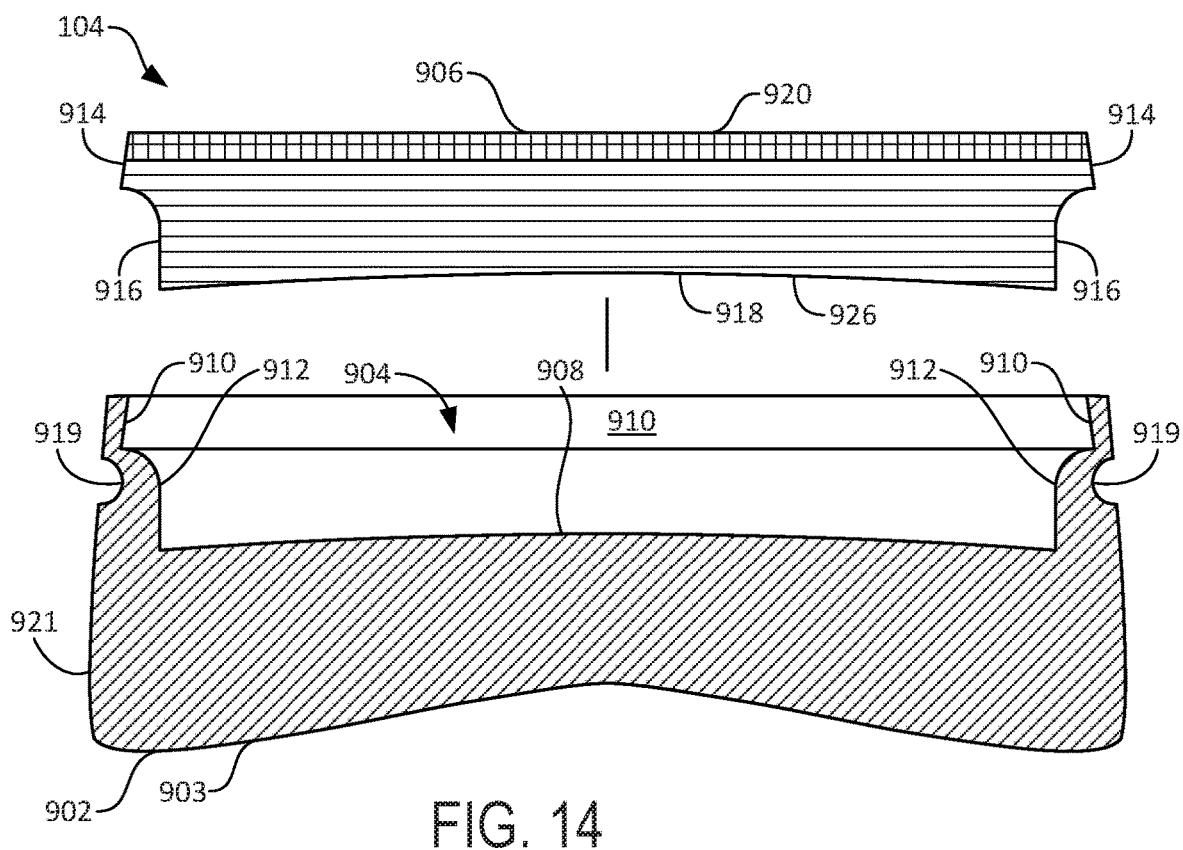
FIG. 14 illustrates a partially exploded front sectional view of the sole along line 13-13 of FIG. 9.

Referring specifically to FIGS. 3, 4, and 8, the lateral side brace 122 and the medial side brace 124 are configured to be disposed distal relative to the ankle and inferiorly relative to the calf. The lateral side brace 122 and the medial side brace 124 are configured to decelerate the foot of the wearer during heel strike and lift the foot of the wearer during propulsion.

In some embodiments, the lateral side brace 122 and the medial side brace 24 may be coupled to the intermediate layer 116 in various manners, such as via an adhesive, ultrasonic welding, melt bonding, and the like (not shown). In other embodiments, the lateral side brace 122 and the medial side brace 124 may be formed from one or more of the inner layer 114, the intermediate layer 116, and the outer layer 118 (not shown). In either case, the lateral side brace 122 and the medial side brace 124 may be formed of a semi-rigid material. The lateral side brace 122 and the medial side brace 124 may be formed of one or more materials having an elastic modulus in a range of 0.5 to 4.6 GPa, more specifically in a range of 1.8 to 4.6 GPa, and more specifically in a range of 3.2 to 4.6 GPa. As a specific example, the lateral side brace 122 and the medial side brace 124 may be formed of a polymer, such as a polymer foam or a rubber.

In some embodiments, and as shown in the figures, the lateral side brace 122 and the medial side brace 124 each have a chevron-like shape, and the lateral side brace 122 and the medial side brace 124 couple to the intermediate layer 116 at the ends 132, 134 of the chevron-like shape and the vertex 136 of the chevron-like shape. Stated another way, the lateral side brace 122 and the medial side brace 124 each include a side brace first portion 138 that extends anteriorly and inferiorly away from the first end 132 and the posterior brace 120 and toward the vertex 136 and the opening 110. The first portion 138 may be disposed at an angle, $\alpha$ (see FIG. 3), in a range of 20 degrees to 90 degrees relative to a horizontal plane (that is, a plane that extends horizontally when the article of footwear 100 is positioned upright on an external horizontal surface). In some embodiments, the angle $\alpha$ differs for the lateral side brace 122 and the medial side brace 124. At the vertex 136, the first portion 138 couples to a side brace second portion 140. The second portion 140 extends posteriorly and inferiorly away from the vertex 136 and the first portion 138 and toward the second end 134 and the posterior brace 120. The second portion 140 may be disposed at an angle, $\beta$ (see FIG. 3), in a range of 20 degrees to 90 degrees relative to the horizontal plane. In some embodiments, the angle $\beta$ differs for the lateral side brace 122 and the medial side brace 124.

In some embodiments, the first portion 138 of each of the lateral side brace 122 and the medial side brace 124 has a first flexural modulus, the second portion 140 of each of the lateral side brace 122 and the medial side brace 124 has a second flexural modulus, and the second flexural modulus is less than the first flexural modulus. In these embodiments, the first portion 138 of each of the lateral side brace 122 and the medial side brace 124 is configured to decelerate the foot of the wearer during heel strike, and the second portion 140 of each of the lateral side brace 122 and the medial side brace 124 is configured to lift. In some embodiments, the flexural moduli of the first portions 138 and the second portions 140 differ due to different dimensions and/or materials of the first portions 138 and second portions 140. As a specific example, each first portion 138 has a thickness (that is, a dimension in a medial-lateral extending direction) in a range of 0.5 to 5.0 cm, more specifically in a range of 1.25 to 4.25 cm, and more specifically in a range of about 3.0 to 3.5 cm, and each second portion 140 has a thickness in a range of 0.5 to 5.0 cm, more specifically in a range of 1.25 to 4.25 cm, and more specifically in a range of about 3.0 to 3.5 cm. In some embodiments, the first flexural modulus is in a range of 0.2 to 10 GPa more specifically in a range of 1.8 to 8.4 GPa, and even more specifically in a range of 3.4 to 6.8 GPa, and the second flexural modulus is in a range of 30 to 300 MPa, more specifically in a range of 75 to 225 MPa, and even more specifically in a range of 120 to 180 MPa.

The lateral side brace 122 and the medial side brace 124 may have various other dimensions. In some embodiments, each first portion 138 has a length (that is, a dimension in a direction extending between the first end 132 and the vertex 136) that depends on the overall size of the article of footwear 100. More specifically, a "small" article of footwear 100 may have a length for each first portion 138 in a range of 6 to 12 inches, a "medium" article of footwear 100 may have a length for each first portion 138 in a range of 13 to 16 inches, a "large" article of footwear 100 may have a length for each first portion 138 in a range of 17 to 21 inches, and an "extra large" article of footwear 100 may have a length for each first portion 138 in a range of 21 to 25 inches. In some embodiments, the length of each first portion 138 is custom-specified (for example, in the case of custom-manufactured articles of footwear 100).

In some embodiments, each second portion 140 has a length (that is, a dimension in a direction extending between the vertex 136 and the second end 134) that depends on the overall size of the article of footwear 100. More specifically, a small article of footwear 100 may have a length for each second portion 140 in a range of 6 to 12 inches, a medium article of footwear 100 may have a length for each second portion 140 in a range of 13 to 16 inches, a large article of footwear 100 may have a length for each second portion 140 in a range of 17 to 21 inches, and an extra large article of footwear 100 may have a length for each second portion 140 in a range of 21 to 25 inches. In some embodiments, the length of each second portion 140 is custom-specified (for example, in the case of custom-manufactured articles of footwear 100). In some embodiments, the length of each first portion 138 and the length of each second portion 140 are specified in view of each other. More specifically, the length of each first portion 138 may be 20 to 50 percent greater than the length of each second portion 140. In some embodiments, the lateral side brace 122 and the medial side brace 124 each have a width (that is, a dimension in a direction perpendicular to both the length and the thickness) in a range of 0.2 to 1.0 cm, more specifically in a range of 0.33 to 0.87 cm, and even more specifically in a range of 0.45 to 0.75 cm. The width of each first portion 138 may differ from the width of each second portion 140.

In some embodiments, and as shown in the figures, the main body 106 may also include a base layer 142 disposed inwardly of the lateral side brace 122 and the medial side brace 124. In some embodiments, the base layer 142 may be continuous or monolithically formed with the inner layer 114. In other embodiments, the base layer 142 may be coupled to the inner layer 114 in other manners, such as stitching, adhesives, and the like (not shown). The base layer 142 may be formed of one or more materials having a static coefficient of friction against steel in range of 0.01 to 1.5, more specifically in range of 0.01 to 1.0, and even more specifically in a range of 0.01 to 0.5. As a specific example, the base layer 142 may be formed of a polymer, such as a synthetic rubber, for example polychloroprene or neoprene. In some embodiments, the base layer 142 may by formed of a material having an air permeability similar to that of polychloroprene neoprene. In some embodiments, the base layer 142 includes a base layer first portion 144 disposed superiorly relative to each side brace first portion 138, a base layer second portion 146 disposed between each side brace first portion 138 and each side brace second portion 140, and a base layer third portion 148 disposed inferiorly relative to each side brace second portion 140.

Referring specifically to FIG. 5, the opening 110 includes a superior portion 150 that is not selectively enclosed by the closure 112. The superior portion 150 couples to an anterior portion 152, which extends from the superior portion 150 to the vamp 154 of the upper 102. The anterior portion 152 couples to an inferior portion 156 formed on the vamp 154 of the upper 102.

Referring specifically to FIGS. 1, 2, 3, 5, and 7, the closure 112 is movably coupled the main body 106 to selectively enclose the anterior portion 152 and the inferior portion 156 of the opening 110. In some embodiments, the closure 112 includes a multiple-piece structure. More specifically and as shown in the figures, the closure 112 includes an anterior portion 158 that selectively encloses the anterior portion 152 of the opening 110 and a superior portion 160 that selectively encloses the superior portion 156 of the opening 110. The anterior portion 158 and the superior portion 160 are separately movable relative to the main body 106 of the upper 102. In other embodiments, the anterior portion 158 and the superior portion 160 are continuous and monolithically formed and movable together relative to the main body 106 (not shown).

In some embodiments, and as shown in the figures, the closure 112 is hingedly coupled to the main body 106. In other embodiments, the closure 112 is coupled to the main body 106 in other manners. For example, the closure 112 may be detachably coupled to the main body 106 (not shown).

The closure 112 and/or the main body 106 of the upper 102 may carry one or more restraining mechanisms to selectively hold the closure 112 in a position to enclose the opening 110. In some embodiments, the restraining mechanisms are adjustable mechanisms to account for bandages and/or swelling of the leg of the wearer. For example, and as shown in the figures, the closure 112 and the main body 106 carry hook-and-loop fasteners 162 to selectively hold the closure 112 in a position to enclose the opening 110. In other embodiments, the restraining mechanisms take other forms. For example, the restraining mechanisms may be non-adjustable mechanisms, such as snap fasteners (not shown).

Figure 7:
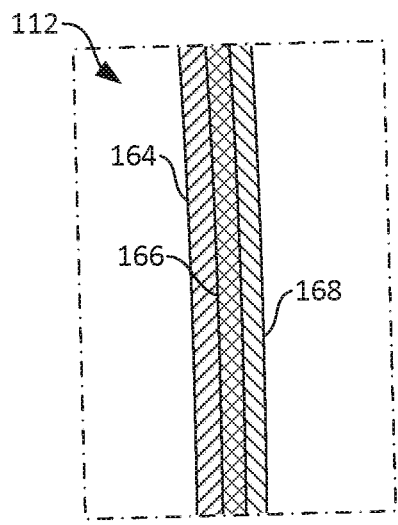
FIG. 7 illustrates a detail view of the article of footwear within line 7-7 of FIG. 5.

Referring specifically to FIGS. 5 and 7, in some embodiments the anterior portion 158 of the closure 112 includes multiple layers. More specifically, in some embodiments, the anterior portion 158 includes an inner layer 164, an intermediate layer 166 disposed outwardly of the inner layer 164, and an outer layer 168 disposed outwardly of the intermediate layer 166. The inner layer 164 may be a breathable, low-friction material. The inner layer 164 may be formed of one or more materials having a static coefficient of friction against steel in range of 0.01 to 1.5, more specifically in range of 0.01 to 1.0, and even more specifically in a range of 0.01 to 0.5. As a specific example, the inner layer 164 may be formed of a polymer, such as a synthetic rubber, for example polychloroprene or neoprene. In some embodiments, the inner layer 164 may be formed of a material having an air permeability similar to that of polychloroprene or neoprene. The superior portion intermediate layer 166 may be a semi-rigid material. The intermediate layer 166 may be formed of one or more materials having an elastic modulus in a range of 0.5 to 4.6 GPa, more specifically in a range of 1.8 to 4.6 GPa, and more specifically in a range of 3.2 to 4.6 GPa. As a specific example, the intermediate layer 166 may be formed of a polymer, such as a polymer foam or a rubber. The superior portion outer layer 168 may be formed of one or more of various materials that may provide various aesthetic and/or function characteristics (for example, water resistance), such as polymers (for example, rubber), fabrics, and/or leather.

Referring again to FIGS. 1, 2, 3, 5, and 7, in some embodiments the anterior portion 158 of the closure 112 includes a superior brace 170 that is configured to support the patellar tendon or the tibial tuberosity of the leg of the wearer. As such, the superior brace 170 reduces forces acting on the foot in stance and gate. In some embodiments, the superior brace 170 is defined by the inner layer 164, the intermediate layer 166, and the outer layer 168 of the anterior portion 158. In some embodiments, and as shown in the figures, the inner layer 164, the intermediate layer 166, and the outer layer 168 of the anterior portion 158 include a concave surface, or a notch, that defines the superior brace 170.

In some embodiments, when the anterior portion 158 of the closure 112 encloses the anterior portion 152 of the opening 110 and is secured to the main body 106 of the upper 102, the upper 102 acts as a substantially rigid unit. This significantly reduces the forces acting on the foot in stance and gate.

Referring specifically again to FIGS. 5 and 7, in some embodiments the superior portion 160 of the closure 112 includes multiple layers. More specifically, the superior portion 160 includes an inner layer 172 and an outer layer 174 disposed outwardly of the inner layer 172. The inferior portion inner layer 172 may be a breathable, low-friction material. The inner layer 172 may be formed of one or more materials having a static coefficient of friction against steel in range of 0.01 to 1.5, more specifically in range of 0.01 to 1.0, and even more specifically in a range of 0.01 to 0.5. As a specific example, the inner layer 172 may be formed of a polymer, such as a synthetic rubber, for example polychloroprene or neoprene. In some embodiments, the inner layer 172 may be formed of a material having an air permeability similar to that of polychloroprene or neoprene. The inferior portion outer layer 174 may be formed of one or more of various materials that may provide various aesthetic and/or function characteristics (for example, water resistance), such as polymers (for example, rubber), fabrics, and/or leather.

Sole

The sole 104 may couple to the upper 102 in various manners, for example, via adhesives or the like. Referring now to FIGS. 9-14, the sole 104 generally includes an outsole 902 that is configured to engage the ground. The outsole 902 includes a body 903 that defines a cavity 904, and the body 903 carries an insole 906 within the cavity 904. The insole 906 is configured to support the foot of the wearer.

The outsole 902 may be formed of one or more materials that facilitate shock absorption and slip inhibition, such as a polymer, more specifically a rubber. In some embodiments, the outsole 902 includes a substantially rigid rocker structure at a metatarsal portion. In some embodiments, such materials and structures may reduce pressure acting on the foot during heel strike and propulsion and decrease the amount of time the foot spends on the heel and in the metatarsal head area.

In some embodiments, the cavity 90 of the outsole 902 has a depth sufficient to completely receive the insole 906. In these embodiments, the insole 906 does not occupy any of the volume of the chamber 108 of the upper 102.

In some embodiments, the cavity 904 of the outsole 902 is defined by a cavity inferior surface 908 and a cavity side surface 910. The cavity side surface 910 of the cavity 904 is dimensioned, together with the dimensions of the insole 906, to interference fittingly engage the insole 906 and secure the insole 906 to the outsole 902. As used herein, "interference fitting engagement" refers to engagement at an interface between an outwardly disposed component and an inwardly disposed component wherein a dimension of the outwardly disposed component is substantially equal to (that is, equal to ±5 percent) a dimension of the inwardly disposed component or less than the dimension of the inwardly disposed component. In some embodiments, the interference fitting engagement between the outsole 902 and the insole 906 permits the outsole 902 and the insole 906 to cooperate as a substantially rigid unit (that is, to inhibit movement of the insole 906 relative to the outsole 902), thereby making appropriate contact with the foot and reducing forces acting on the foot in stance and gate.

In some embodiments, interference fitting engagement between the outsole 902 and the insole 906 is provided by a securing structure formed the outsole 902 and/or the insole 906. In some embodiments, the securing structure includes one or more protrusions 912 formed on the outsole 902 and/or the insole 906, and the protrusions 912 engage the other of the outsole 902 and the insole 906 to secure the insole 906 to the outsole 902. In some embodiments, and as shown in the figures, the cavity side surface 910 forms the protrusion 912. In addition, a side surface 914 of the insole 906 includes a recess 916 for engaging the protrusion 912. In some embodiments, and as shown in the figures, the protrusion 912 and the recess 916 have arcuate surfaces. In other embodiments, the protrusion 912 and the recess 916 have other shapes. For example, the protrusion 912 and the recess 916 may include flat sides (not shown). In some embodiments, and as shown in the figures, the protrusion 912 extends about the entire periphery of the cavity 904 and the recess 916 extends about the entire periphery of the insole side surface 914.

Interference fitting engagement and/or the securing structure may be provided in various other manners. For example, the cavity side surface 910 may form the recess 916 and the insole side surface 914 may form the protrusion 912 (not shown). As another example, the cavity surface 910 may form the protrusion 912, and the protrusion 912 may engage an insole side surface 914 that is flat (not shown). As another example, the insole side surface 914 may form the protrusion 912, and the protrusion 912 may engage a cavity side surface 910 that is flat (not shown). As yet another example, the protrusion 912 extends about less than the entire periphery of the cavity 904 (not shown), or multiple protrusions 912 extend about different portions of the periphery of the cavity 904 (not shown). As yet another example, the recess 916 extends about less than the entire periphery of the insole side surface 914 (not shown), or multiple recesses 916 extend about different portions of the periphery of the insole side surface 914 (not shown). As a further example, interference fitting engagement and/or the securing structure may be provided by features formed on the cavity inferior surface 908 and an inferior surface 918 of the insole 906.

In some embodiments, and as shown in the figures, the outsole 902 includes a channel 919 extending about at least a portion of the perimeter of the outer side surface 921. The channel 919 may be formed as a result of deforming the outsole 902 to provide the protrusion 912 and/or to provide the outsole 902 with the appearance of being a multiple component structure.

In some embodiments, the insole 906 is configured to offload the heel, the metatarsal head, and the forefoot when standing and walking. The insole 906 is configured to rapidly transition the foot to propulsion.

In some embodiments, the insole 906 includes various layers and/or portions having different functional characteristics and/or features. As a specific example, and as shown in the figures, the insole 906 includes a cloth superior layer 920 that has antibacterial and antifungal properties. Inferiorly of the superior layer 920, the insole 906 includes a heel portion. The heel portion 922 includes a shock absorbing material, such as a viscoelastic polymer, more specifically a thermoset, polyether-based, polyurethane, such as, for example, Sorbothane® available from Sorbothane, Incorporated of Kent, Ohio. The heel portion 922 may be a Heel Defender™ available from Heel-It of South Miami, Fla. Anteriorly of the heel portion 922, the insole 906 includes a forefoot portion 924. The forefoot portion 924 includes a shock absorbing material, such as a viscoelastic polymer, more specifically a thermoset, polyether-based, polyurethane, such as, for example, Sorbothane®. The forefoot portion 924 may be a Forefoot Defender™ available from Heel-it. Anteriorly of the forefoot portion 924, the insole 906 includes a toe portion 926. The toe portion 926 includes a relatively soft material, such as a closed cell cross-linked polyethylene foam, for example, Plastazote® available from Zotefoams of the United Kingdom. Inferiorly of the heel portion 922 and the forefoot portion 924, the insole 906 includes a substantially rigid inferior layer 928.

Figure 15:
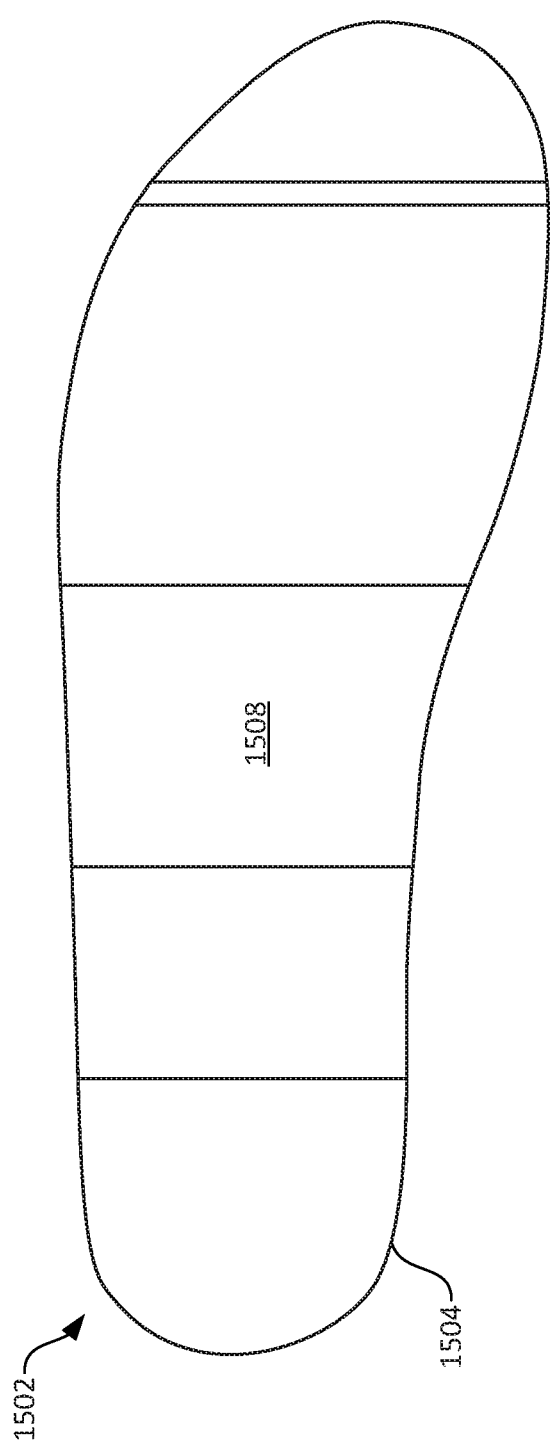
FIG. 15 illustrates a top view of an embodiment of an insole of an article of footwear according to the present disclosure.
Figure 16:
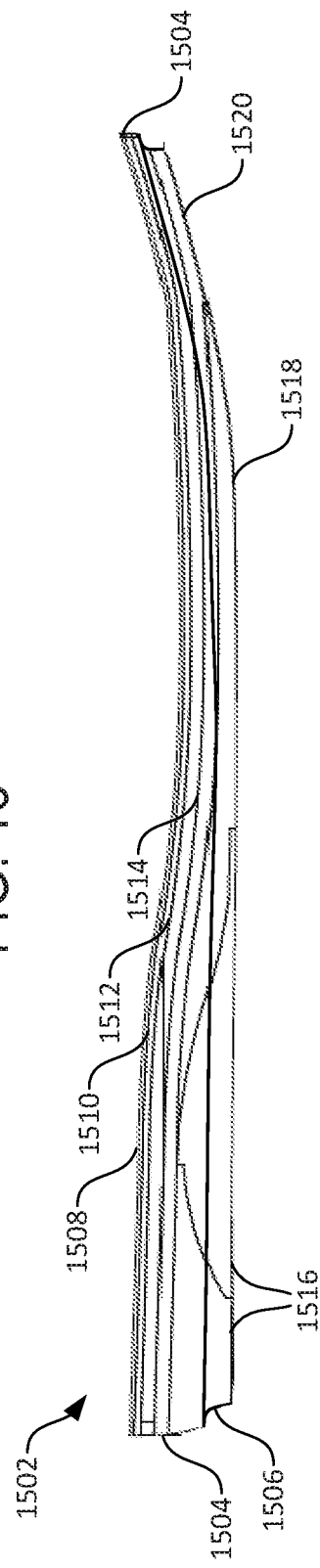
FIG. 16 illustrates a medial side view of the insole of FIG. 15.

Embodiments of insoles according to the present disclosure may take various other forms. For example, and referring now to FIGS. 15 and 16, another embodiment of an insole 1502 is illustrated. A side surface 1504 of the insole 1502 includes a recess 1506 for engaging the protrusion within the outsole cavity. The insole 1502 further includes a cloth superior layer 1508 that has antibacterial and antifungal properties. Below the superior layer 1508, the insole 1502 includes a first intermediate layer 1510, which is a relatively soft material, such as a closed cell cross-linked polyethylene foam, for example, Plastazote®. Inferiorly of the first intermediate layer 1510, the insole 1502 includes a second intermediate layer 1512, which includes a shock-absorbing material, such as a microcellular urethane, for example, PORON® available from Rogers Corporation of Rogers, Conn. Inferiorly of the second intermediate layer 1512, the insole 1502 includes a third intermediate layer 1514, which is a relatively soft material, such as a closed cell cross-linked polyethylene foam, for example, Plastazote®. Inferiorly of the third intermediate layer 1514, the insole 1502 includes a heel portion 1516. The heel portion 1516 includes a shock absorbing material, such as a viscoelastic polymer, more specifically a thermoset, polyether-based, polyurethane, such as, for example, Sorbothane®. The heel portion 1516 may be a Heel Defender™. Anteriorly of the heel portion 1516, the 1502 includes a forefoot portion 1518. The forefoot portion 1518 includes a shock absorbing material, such as a viscoelastic polymer, more specifically a thermoset, polyether-based, polyurethane, such as, for example, Sorbothane®. The forefoot portion 1518 may be a Forefoot Defender™. Anteriorly of the forefoot portion 1518, the insole 1502 includes a toe portion 1520. The toe portion 1520 includes relatively soft material, such as a closed cell cross-linked polyethylene foam, for example, Plastazote®.

As another example, in some embodiments the insole may include any of the orthotic devices described in U.S. Patent Application Publication No 2015/0047221 the disclosure of which is hereby incorporated by reference.

Figure 17:
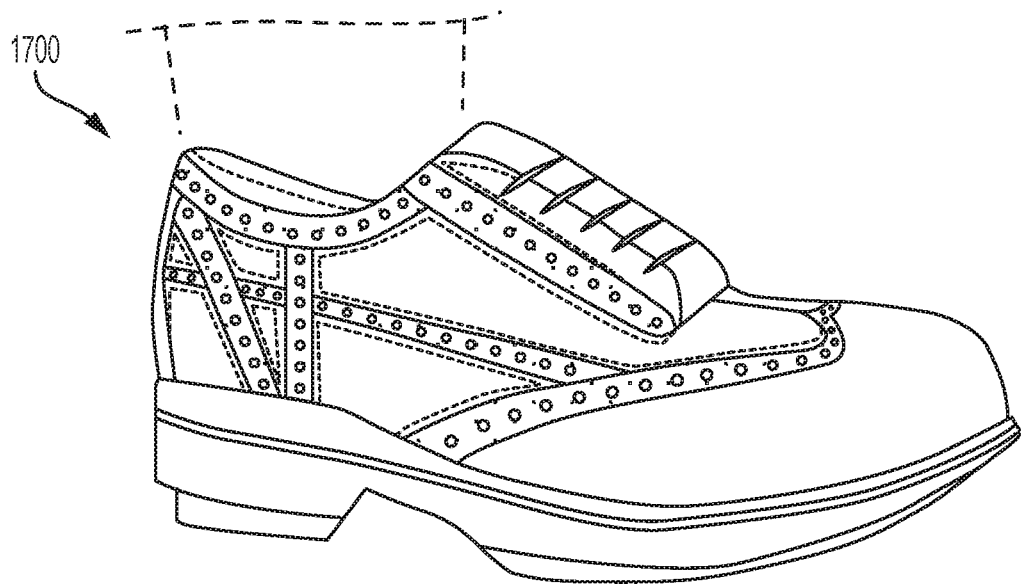
FIG. 17 illustrates a front perspective view of another embodiment of an article of footwear according to the present disclosure.
Figure 18:
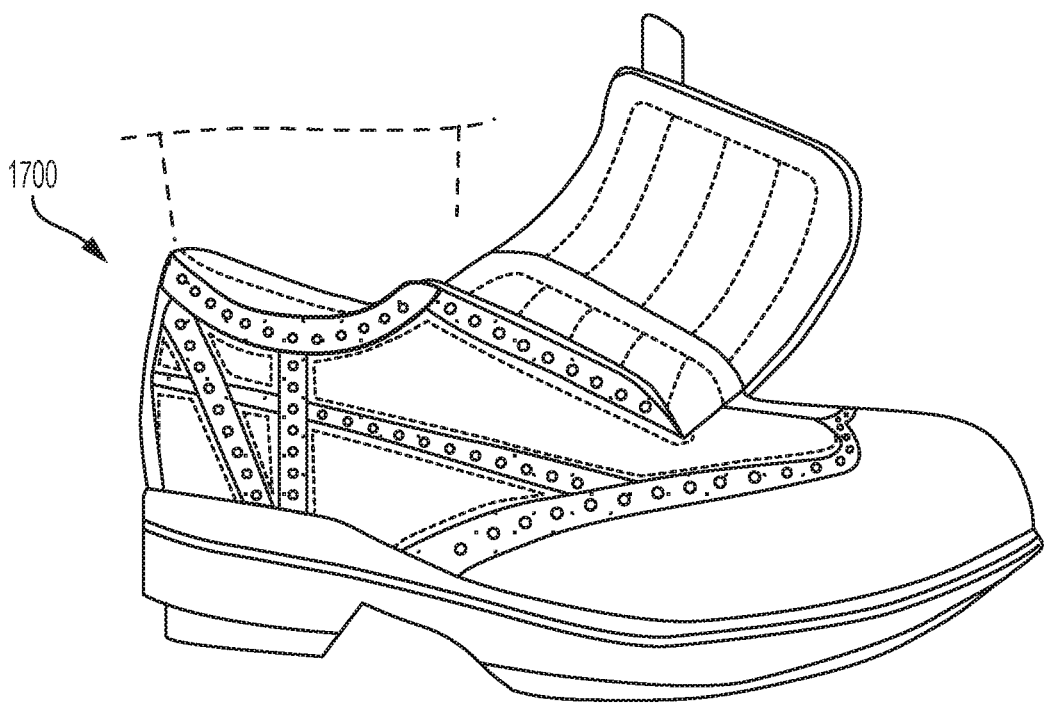
FIG. 18 illustrates another front perspective view of the article of footwear of FIG. 17 with a superior closure in an open position.
Figure 19:
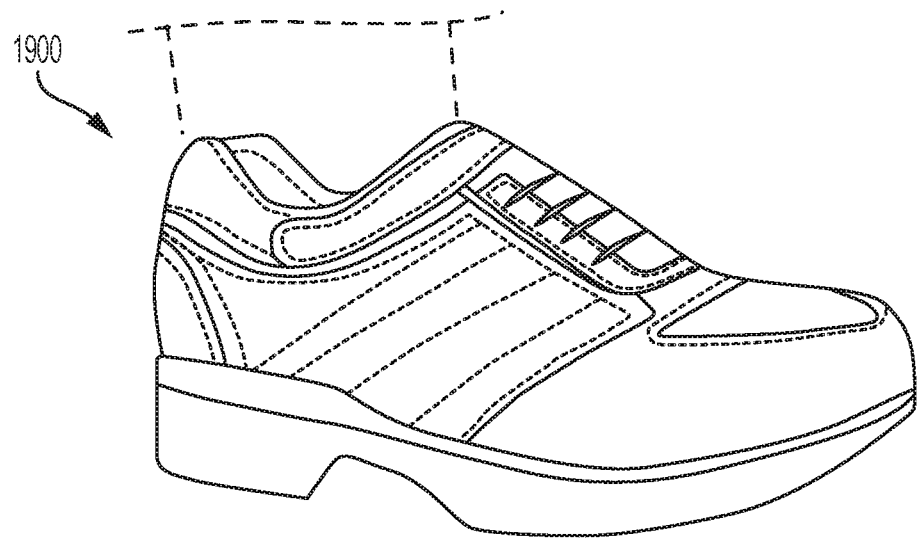
FIG. 19 illustrates a front perspective view of another embodiment of an article of footwear according to the present disclosure.
Figure 20:
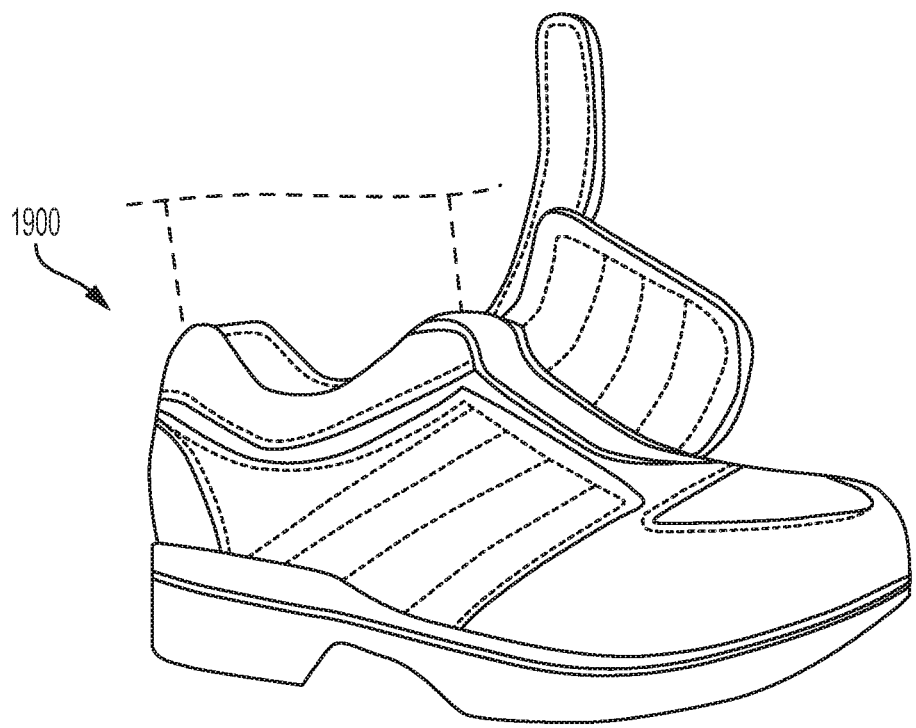
FIG. 20 illustrates another front perspective view of the article of footwear of FIG. 19 with a superior closure in an open position.

Articles of footwear according to embodiments of the present disclosure may be provided in various styles and/or with various aesthetically pleasing features. For example, and referring to FIGS. 17 and 18, an article of footwear 1700 according to an embodiment of the present disclosure is formed in the style of a dress shoe. The article of footwear 1700 may include any of the embodiments of the upper and/or the sole described herein. As another example and referring to FIGS. 19 and 20, an article of footwear 1900 according to an embodiment of the present disclosure is formed in the style of a casual shoe. The article of footwear 1900 may include any of the embodiments of the upper and/or the sole described herein.

Articles of footwear according to embodiments of the present disclosure may differ from the embodiments described above in various other manners. For example, the upper could include one of the lateral side brace and the medial side brace. As another example, the closure could be formed on a posterior side of the upper, and the superior brace could be formed on the main body of the upper. In some embodiments, the sole lacks an adhesive coupling the insole to the outsole. In some embodiments, the article of footwear lacks a closure that extends partially from the tibial tuberosity to the toe.

Articles of footwear according to embodiments of the present disclosure may include various materials in addition to or as alternatives to the materials described above. For example, articles of footwear according to embodiments of the present disclosure may include leather, synthetics, plastics, nylon, rubber, cloth, foam, felt, fabric, GORE-TEX®, materials manufactured by Vibram of Albizzate, Italy, Thinsulate™, CORDURA® fabric, CAMBRELLE®, paper, wood, lace, and/or any other materials commonly used for articles of footwear and/or orthopedic devices.

Articles of footwear according to embodiments of the present disclosure may be manufactured using various methods. For example, articles of footwear according to embodiments of the present disclosure may be custom manufactured based on the medical condition of a specific wearer. More specifically, articles of footwear according to embodiments of the present disclosure may be custom manufactured using any of the methods described in U.S. Pat. No. 9,201,413, the disclosure of which is hereby incorporated by reference. As another example, articles of footwear according to embodiments of the present disclosure may be may mass manufactured in various sizes to accommodate the legs of different types of wearers. More specifically, articles of footwear may be sized in accordance with any common footwear size system, such as those used in the United States, the United Kingdom, or the like.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

What is claimed is:

1. An article of footwear configured to be worn on a lower leg and foot of a wearer, comprising:
    an upper comprising a main body, the main body comprising:
        a posterior brace configured to be disposed posteriorly relative to the lower leg of the wearer, the posterior brace configured to stabilize the heel of the wearer;
        at least one side brace coupled to the posterior brace, the side brace configured to be disposed medially or laterally relative to the lower leg of the wearer, the side brace having portions formed of a semi-rigid material adapted to decelerate the foot of the wearer during heel strike;
    a sole coupled to the upper, the sole including an outsole and an insole, the outsole configured to engage the ground and having a body defining a cavity, the insole configured to support the foot of the wearer, the insole interference fittingly engaging the outsole in the cavity to secure the insole to the outsole, and the cavity configured to house the insole.

2. The article of footwear of claim 1, wherein the upper further comprises a superior brace configured to support the patellar tendon or the tibial tuberosity of the leg of the wearer.

3. The article of footwear of claim 1, wherein the upper comprises:
    an inner layer comprising a breathable, low-friction material;
    an intermediate layer disposed outwardly of the inner layer, and the intermediate layer comprising a semi-rigid material; and
    an outer layer disposed outwardly of the intermediate layer.

4. The article of footwear of claim 1, wherein the side brace comprises:
    a first portion extending anteriorly and inferiorly away from the posterior brace; and
    a second portion coupled to the first portion, the second portion extending posteriorly and inferiorly away from the first portion at a vertex, with such portions forming a chevron-like shape.

5. The article of footwear of claim 4, wherein the first portion is disposed at a first angle between a first end and the vertex, with such first angle having a range of 20 degrees to 90 degrees relative to the horizontal plane; and the second portion is disposed at a second angle between a second end and the vertex, with such second angle having a range of 20 degrees to 90 degrees relative to the horizontal plane.

6. The article of footwear of claim 4, wherein the upper further comprises a flexible material disposed inwardly of the side brace, the flexible material comprising:
    a first portion disposed superiorly relative to the first portion of the side brace;
    a second portion disposed between the first portion of the side brace and the second portion of the side brace; and
    a third portion disposed inferiorly relative to the second portion of the side brace.

7. The article of footwear of claim 1, wherein at least one of the outsole and the insole form a securing structure, the securing structure comprising a protrusion for engaging the other of the outsole and the insole and securing the insole to the outsole.

8. The article of footwear of claim 1, wherein at least one of the outsole and the insole comprise a protrusion interference fittingly engaging the other of the outsole and the insole to secure the insole to the outsole.

9. An article of footwear configured to be worn on a lower leg and foot of a wearer, comprising:
an upper comprising:
a posterior brace configured to be disposed posteriorly relative to the lower leg of the wearer, the posterior brace configured to stabilize the heel of the wearer;
a superior brace coupled to the posterior brace, the superior brace configured to support the patellar tendon or the tibial tuberosity of the leg of the wearer; and
at least one side brace configured to be disposed medially or laterally relative to a lower leg of the wearer, the side brace having portions formed of a semi-rigid material, the side brace further comprising a first portion extending anteriorly and inferiorly away from the posterior brace; and a second portion coupled to the first portion, the second portion extending posteriorly and inferiorly away from the first portion at a vertex, with such portions forming a chevron-like shape adapted to decelerate the foot of the wearer during heel strike; and
a sole coupled to the upper.

10. The article of footwear of claim 9, wherein:
the first portion is disposed at a first angle between a first end and the vertex, with such first angle having a range of 20 degrees to 90 degrees relative to the horizontal plane; and
the second portion is disposed at a second angle between a second end and the vertex, with such second angle having a range of 20 degrees to 90 degrees relative to the horizontal plane.

11. An article of footwear configured to be worn on a lower leg and foot of a wearer, comprising:
an upper comprising:
a posterior brace configured to be disposed posteriorly relative to the lower leg of the wearer, the posterior brace configured to stabilize the heel of the wearer;
a superior brace coupled to the posterior brace, the superior brace configured to support the patellar tendon or the tibial tuberosity of the leg of the wearer; and
at least one side brace configured to be disposed medially or laterally relative to a lower leg of the wearer, the side brace having portions formed of a semi-rigid material adapted to decelerate the foot of the wearer during heel strike; with such portions comprising: a first portion extending anteriorly and inferiorly away from the posterior brace, with such first portion having a first bending stiffness; and a second portion coupled to the first portion, the second portion extending posteriorly and inferiorly away from the first portion, with such second portion having a second bending stiffness, which is greater than the first bending stiffness; and
a sole coupled to the upper.

12. The article of claim 11, wherein the sole includes an outsole and an insole, the outsole configured to receive the insole, the outsole comprising a body defining a cavity, the body comprising a projection extending into the cavity and being sized to interference fittingly engage the insole to secure the insole to the outsole.

13. The article of footwear of claim 12, wherein the projection comprises an arcuate surface.

14. An article of footwear configured to be worn on a lower leg and foot of a wearer, comprising:
an upper comprising a main body, the main body comprising:
a posterior brace configured to be disposed posteriorly relative to the lower leg of the wearer, the posterior brace configured to stabilize the heel of the wearer;
at least one side brace coupled to the posterior brace, the side brace configured to be disposed medially or laterally relative to the lower leg of the wearer, the side brace having portions formed of a semi-rigid material adapted to decelerate the foot of the wearer during heel strike, and wherein the side brace further comprises:
a first portion extending anteriorly and inferiorly away from the posterior brace, and which has a first flexural modulus; and
a second portion coupled to the first portion, the second portion extending posteriorly and inferiorly away from the first portion, and which has a second flexural modulus being less than the first flexural modulus; and
a sole coupled to the upper, the sole including an outsole and an insole, the outsole configured to engage the ground and having a body defining a cavity, the insole configured to support the foot of the wearer, the insole interference fittingly engaging the outsole in the cavity to secure the insole to the outsole.

15. The article of footwear of claim 1, wherein the insole is secured within the outsole.

* * * * *